United States Patent
Uchida et al.

(10) Patent No.: US 11,650,196 B2
(45) Date of Patent: May 16, 2023

(54) BLOOD COAGULATION SYSTEM ANALYSIS APPARATUS, BLOOD COAGULATION SYSTEM ANALYSIS SYSTEM, BLOOD COAGULATION SYSTEM ANALYSIS METHOD, BLOOD COAGULATION SYSTEM ANALYSIS PROGRAM, BLOOD LOSS PREDICTION APPARATUS, BLOOD LOSS PREDICTION SYSTEM, BLOOD LOSS PREDICTION METHOD, AND BLOOD LOSS PREDICTION PROGRAM

(71) Applicant: Sony Corporation, Tokyo (JP)

(72) Inventors: Tokujiro Uchida, Kanagawa (JP);
Yudai Yamamoto, Tokyo (JP);
Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 957 days.

(21) Appl. No.: 16/474,745

(22) PCT Filed: Oct. 18, 2017

(86) PCT No.: PCT/JP2017/037694
§ 371 (c)(1),
(2) Date: Jun. 28, 2019

(87) PCT Pub. No.: WO2018/128002
PCT Pub. Date: Jul. 12, 2018

(65) Prior Publication Data
US 2019/0346425 A1    Nov. 14, 2019

(30) Foreign Application Priority Data

Jan. 6, 2017  (JP) .............................. JP2017-001011

(51) Int. Cl.
| | | |
|---|---|---|
| *G01N 33/86* | (2006.01) | |
| *G01N 33/49* | (2006.01) | |
| *G16B 5/20* | (2019.01) | |
| *G01N 27/02* | (2006.01) | |

(52) U.S. Cl.
CPC ......... *G01N 33/4905* (2013.01); *G01N 33/86* (2013.01); *G16B 5/20* (2019.02); *G01N 27/02* (2013.01)

(58) Field of Classification Search
CPC ........ G01N 27/02; G01N 27/22; G01N 33/49; G01N 33/4905; G01N 33/86; G16B 5/20
USPC ......... 702/19; 436/63, 69, 149, 150; 422/73; 422/82.01, 82.02; 435/13; 73/64.41; 600/369

See application file for complete search history.

(56) References Cited

U.S. PATENT DOCUMENTS

| | | | | |
|---|---|---|---|---|
| 7,021,122 | B1* | 4/2006 | Rosemberg | G01N 11/04 73/304 C |
| 8,735,163 | B2* | 5/2014 | Hayashi | G01N 33/86 436/63 |
| 9,518,997 | B2* | 12/2016 | Hayashi | G01N 33/86 |
| 10,281,452 | B2* | 5/2019 | Hayashi | G01N 27/06 |
| 2003/0064414 | A1 | 4/2003 | Benecky et al. | |
| 2017/0030891 | A1* | 2/2017 | Brun | G01N 33/4905 |

FOREIGN PATENT DOCUMENTS

| | | |
|---|---|---|
| EP | 3133390 A1 | 2/2017 |
| JP | 2003-505678 A | 2/2003 |
| JP | 2004522146 A | 7/2004 |
| JP | 2008191171 A | 8/2008 |
| JP | 2010-181400 A | 8/2010 |
| JP | 2012-194087 A | 10/2012 |
| JP | 2015-206609 A | 11/2015 |
| WO | WO 01/07070 A1 | 2/2001 |
| WO | WO 02/079375 A1 | 10/2002 |
| WO | WO 2015/159623 A1 | 10/2015 |
| WO | 2015/159623 A1 | 4/2017 |

OTHER PUBLICATIONS

International Search Report and English translation thereof dated Dec. 19, 2017 in connection with International Application No. PCT/JP2017/037694.
Hasegawa et al., Novel Dielectric Coagulometer Identifies Hypercoagulability in Patients with a High CHADS?. Score Without Atrial Fibrillation, PLOS One, Jun. 8, 2016, vol. 11, No. 6, pp. 1-16.
Hayashi et al., Principles of Diaelectric Blood Coagulometry as a Comprehensive Coagulation Test, Analytical Chemistry, 2015, vol. 87, pp. 10072-10079.
Romlin, B., Monitoring of Coagulation and Platelet Function in Paediatric Cardiac Surgery, 2013 [retrieved on Dec. 7, 2017] https://gupea.ub.gu.se/bitstream/2077/33114/1/gupea_2077_33114_1.pdf, pp. 1-75.

(Continued)

*Primary Examiner* — Maureen Wallenhorst
(74) *Attorney, Agent, or Firm* — Wolf, Greenfield & Sacks, P.C.

(57) ABSTRACT

A blood coagulation system analysis apparatus includes: an estimating unit that estimates a characteristic regarding an inhibitor of a blood coagulation factor on a basis of a comparison result between a first result regarding a blood coagulation inhibition ability of the inhibitor of the blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from the concentration of the blood coagulation factor in the first blood sample or does not contain any blood coagulation factor.

15 Claims, 6 Drawing Sheets

(56) References Cited

OTHER PUBLICATIONS

International Written Opinion and English translation thereof dated Dec. 19, 2017 in connection with International Application No. PCT/JP2017/037694.

International Preliminary Report on Patentability and English translation thereof dated Jul. 18, 2019 in connection with International Application No. PCT/JP2017/037694.

* cited by examiner

BLOOD COAGULATION SYSTEM ANALYSIS APPARATUS, BLOOD COAGULATION SYSTEM ANALYSIS SYSTEM, BLOOD COAGULATION SYSTEM ANALYSIS METHOD, BLOOD COAGULATION SYSTEM ANALYSIS PROGRAM, BLOOD LOSS PREDICTION APPARATUS, BLOOD LOSS PREDICTION SYSTEM, BLOOD LOSS PREDICTION METHOD, AND BLOOD LOSS PREDICTION PROGRAM

CROSS-REFERENCE TO RELATED APPLICATIONS

This application claims the benefit under 35 U.S.C. § 371 as a U.S. National Stage Entry of International Application No. PCT/JP2017/037694, filed in the Japanese Patent Office as a Receiving Office on Oct. 18, 2017, which claims priority to Japanese Patent Application Number JP2017-001011, filed in the Japanese Patent Office on Jan. 6, 2017, each of which is hereby incorporated by reference in its entirety.

TECHNICAL FIELD

The present technology relates to a blood coagulation system analysis apparatus, a blood coagulation system analysis system, a blood coagulation system analysis method, a blood coagulation system analysis program, a blood loss prediction apparatus, a blood loss prediction system, a blood loss prediction method, and a blood loss prediction program.

BACKGROUND ART

Thrombogenesis (coagulation) and thrombolysis (fibrinolysis) in vivo progress by a complex cascade reaction. Both of numerous molecular components including coagulation factors, fibrinogen, fibrin and the like, and cell components such as vascular endothelial cells and blood platelets are involved in the reaction. In treatment or prevention of diseases and injuries involving the coagulation and the fibrinolysis, various tests are performed in order to ascertain a blood coagulation ability and a fibrinolytic ability of a patient. These tests can be roughly classified into quantitative tests for measuring amounts of specific molecules involved in coagulation/fibrinolytic reaction systems such as various coagulation factors, fibrinogen, and D-dimer, and function tests for evaluating a degree of activity of the entirety or a part of the reaction system.

Examples of widely prevalent function tests can include a prothrombin time (PT) test and an activated partial thromboplastin time (APTT) test. The PT test and the APTT test are function tests of an extrinsic coagulation ability and an intrinsic coagulation ability, respectively. In these tests, substances (for example, tissue factor and ellagic acid, respectively) which cause an extrinsic coagulation reaction and an intrinsic coagulation reaction, respectively, are significantly excessively added, such that test results can be obtained in a short time. Normal values of PT and APTT are approximately 10 seconds and 30 to 40 seconds, respectively. These tests are suitable for evaluating a remarkable decrease in a coagulation ability, that is, a bleeding tendency.

In addition, examples of other function tests can include thromboelastography and thromboelastometry. TEG 5000 (Haemonetics Corporation) and ROTEM delta (Tem Innovations GmbH) have been put to practical use as apparatuses for these tests, respectively. In the TEG 5000, a whole blood specimen is injected into a cup which is a measurement container, a causing substance is added depending on a test purpose, a rod-shaped pin suspended by a wire from the top of the measurement container is immersed, and a normal reciprocating angular motion (typically a motion that reciprocates in a range of 4.45 degrees for 10 seconds) is given to the measurement container. As a coagulation reaction progresses, viscoelasticity of the specimen is increased, and a relative motion between the cup and pin is decreased, such that a rotational displacement of the pin is increased. By recording this rotational displacement over time using an optical system in the apparatus, a waveform called a thromboelastogram is obtained. The ROTEM delta is basically based on the same principle even though there is a difference in that a reciprocating angular motion is given to a pin rather than a cup. The PT test and the APTT test are endpoint detection methods for coagulation, while the thromboelastography and the thromboelastometry have an advantage that a series of processes from initiation of coagulation to thrombogenesis and the subsequent fibrinolysis can be monitored over time by a single apparatus. It can be said that the thromboelastography and the thromboelastometry focus on fibrin formation, which is a final stage of a coagulation cascade reaction, and monitor processes of fibrin network formation (coagulation) and thrombolysis (fibrinolysis) through the viscoelasticity of the specimen, thereby comprehensively testing an activity of the entirety of the reaction system until fibrin is formed.

In recent years, as a method capable of more conveniently and accurately evaluating a blood coagulation ability, a method of performing dielectric measurement of a blood coagulation process has been devised (the following Patent Documents 1 and 2). This method is a method of filling blood in a condenser-shaped sample unit including a pair of electrodes, and the like, and applying an alternating current (AC) electric field to the sample unit to measure a change in a permittivity accompanying a blood coagulation process. It has been shown that it is possible to conveniently monitor processes of coagulation and fibrinolysis reactions by using this method (the following Non Patent Document 1).

Technologies related to the above method have also been developed. For example, a blood state analysis apparatus described in the following Patent Document 3 includes a "correcting unit (claim 1) that corrects a blood coagulation evaluation result of the blood sample so as to correspond to a concentration of the drug present in the plasma in the blood sample on the basis of a correlation between the concentration of the drug in the plasma and the blood coagulation evaluation result". In addition, a blood state analysis apparatus described in the following Patent Document 4 includes an "analysis unit (claim 1) that evaluates an influence of the drugs or factors in the blood on a coagulation system or fibrinolysis system of the blood by utilizing change data over time in electrical characteristics measured in a specific frequency or frequency band, with respect to two or more blood samples whose types or concentrations of drugs regulated from one blood specimen are different from each other.

CITATION LIST

Patent Document

Patent Document 1: Japanese Patent Application Laid-Open No. 2010-181400
Patent Document 2: Japanese Patent Application Laid-Open No. 2012-194087

Patent Document 3: Japanese Patent Application Laid-Open No. 2015-206609
Patent Document 4: International Publication No. WO 2015/159623
Non Patent Document 1: Y. Hayashi et al., Analytical Chemistry (19), 10072-10079 (2015)

SUMMARY OF THE INVENTION

Problems to be Solved by the Invention

In surgery using an artificial heart-lung machine, such as cardiac surgery, heparin is generally added to blood to prevent thrombogenesis. Heparin can dramatically increase an ability of antithrombin to inhibit thrombin in the blood, thereby effectively suppressing a coagulation activity. Further, at the time of finishing an operation of the artificial heart-lung machine, by using a heparin neutralizer such as protamine, a coagulation activity to be required can be rapidly recovered. However, it is also known that heparin acts to release a tissue factor pathway inhibitor (hereinafter, also referred to as TFPI) mainly located in the vascular endothelium in the blood. As a concentration of TFPI in the blood is increased, a reaction is suppressed even at a vascular injury portion where a coagulation reaction should originally occur, such that there is a possibility that effective hemostasis cannot be performed. TFPI in the blood cannot be neutralized even with protamine, and the like. For this reason, as the concentration of TFPI in the blood is increased, an unexpected coagulation inhibition state continues. The increase in the concentration of TFPI in the blood may be one of the causes of continuation of postoperative bleeding, or the like. Therefore, there is a clear need for a medical field to quickly and conveniently evaluate the concentration or an activity of TFPI in the blood.

As a method of analyzing the concentration or activity of TFPI in the blood, only analysis of plasma components obtained by centrifugation is currently available. Since this analysis requires time and labor, it has not been implemented as a perioperative clinical test.

The PT test and the APTT test are appropriate for evaluating a remarkable decrease in a coagulation ability, that is, a bleeding tendency, but are not appropriate for evaluating a remarkable increase in a coagulation ability, that is, a thrombotic tendency or a subtle change in a coagulation ability. It is also difficult to evaluate TFPI in the blood by the PT test or the APTT test. As an intraoperative coagulation test, an activated coagulation time (ACT) test is often used, which is particularly effective for monitoring an effect of heparin. However, an ACT test is a test performed using a large amount of substances that cause an intrinsic coagulation pathway, and it is difficult to evaluate TFPI related to subtle regulation and control of an extrinsic coagulation pathway.

It is considered that primary causes of preventing population of the thromboelastography and the thromboelastometry are (1) measurement is not automated and a test result depends on hand skill of a measurer, (2) the thromboelastography and the thromboelastometry are susceptible to vibration, (3) a quality control (QC) procedure is complicated, and a reagent for QC is expensive, (4) skill is required in interpreting an output signal (thromboelastogram), and the like. Further, the thromboelastography and the thromboelastometry do not show a high sensitivity for deficiency or an inhibition effect of each extrinsic or intrinsic coagulation factor, and may be unable to satisfy a need of the medical field.

A main object of the present technology is to provide a technology that enables evaluation of a characteristic of an inhibitor of a blood coagulation factor.

Solutions to Problems

The present inventors have found that it is possible to evaluate a characteristics of an inhibitor of a blood coagulation factor by adding a new component to a blood coagulation system analysis apparatus such as an apparatus described in Patent Document 1 or 2. In addition, the present inventors have also found that it is possible to predict a blood loss by such a component.

That is, the present technology provides a blood coagulation system analysis apparatus including: an estimating unit that estimates a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

The first result and the second result may be rates of change of the electrical characteristic at a point in time when a change over time in the electrical characteristic becomes maximum after blood coagulation starts.

The comparison result may be a ratio between the first result and the second result.

A difference between the concentration of the blood coagulation factor in the blood from which the first result is obtained and the concentration of the blood coagulation factor in the blood from which the second result may be obtained is 0.50 pM or more.

The inhibitor may be a tissue factor pathway inhibitor.

The comparison result may be a result obtained by correcting a ratio between the first result and the second result by a hematocrit value of the blood.

The comparison result may be a result obtained by correcting a ratio between the first result and the second result by a hematocrit value of the blood and a characteristic value regarding an intrinsic coagulation path.

In addition, the characteristic regarding the inhibitor may be a concentration or an activity of the inhibitor.

In addition, the present technology also provides a blood loss prediction apparatus including: a predicting unit that predicts a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

In addition, the present technology also provides a blood coagulation system analysis system including: a blood coagulation system analysis apparatus that includes an estimating unit estimating a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a display apparatus that displays an estimation result.

In addition, the present technology also provides a blood loss prediction system including: a blood loss prediction apparatus that includes a predicting unit predicting a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a display apparatus that displays the predicted blood loss.

In addition, the present technology also provides a blood coagulation system analysis method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of estimating a characteristic regarding the inhibitor on the basis of a comparison result.

In addition, the present technology also provides a blood loss prediction method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of predicting a blood loss of an individual on the basis of a comparison result.

In addition, the present technology also provides a blood coagulation system analysis program for causing a computer to execute: a step of estimating a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

In addition, the present technology also provides a blood loss prediction program for causing a computer to execute: a step of predicting a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

Effects of the Invention

According to the present technology, it is possible to evaluate a characteristic of an inhibitor of a blood coagulation factor. In addition, according to the present technology, it is possible to predict a blood loss. It should be noted that an effect of the present technology is not necessarily limited to an effect described herein, and may be any of the effects described in the present specification.

MODE FOR CARRYING OUT THE INVENTION

Hereinafter, preferred embodiments for carrying out the present technology will be described. It should be noted that embodiments to be described below represent representative embodiments of the present technology, so that a scope of the present technology is not narrowly interpreted by embodiments to be described above. It should be noted that a description will be given in the following order.
1. Blood Coagulation System Analysis Apparatus
(1) Blood Coagulation Factor and Inhibitor of Blood Coagulation Factor
(2) Electrical Characteristic
(3) First Result and Second Result
(4) Comparison result between First Result and Second Result
(5) Estimation of Characteristic regarding Inhibitor
(6) Other Components
2. Blood Loss Prediction Apparatus
3. Blood Coagulation System Analysis System
4. Blood Loss Prediction System
5. Blood Coagulation System Analysis Method
6. Blood Loss Prediction Method
7. Blood Coagulation System Analysis Program
8. Blood Loss Prediction Program
9. Example 1. Blood Coagulation System Analysis Apparatus A blood coagulation system analysis apparatus according to the present technology includes: an estimating unit that estimates a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

Figure 1:
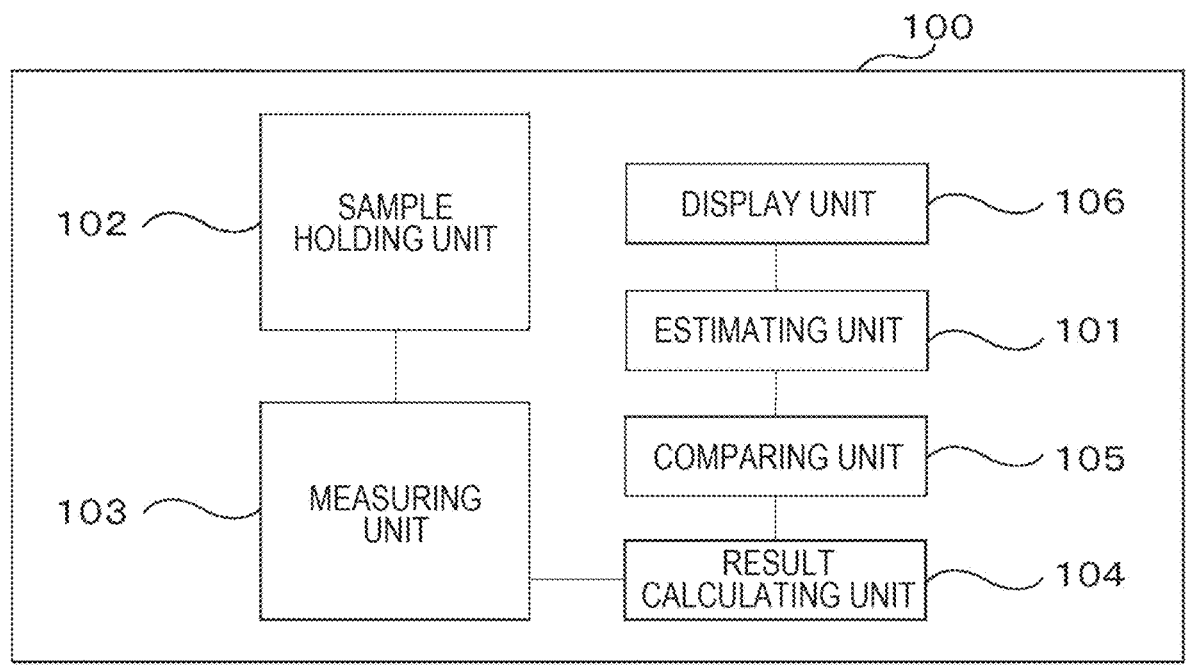
FIG. 1 is a schematic diagram illustrating a configuration of a blood coagulation system analysis apparatus.

FIG. 1 schematically illustrates a configuration of a blood coagulation system analysis apparatus according to the present technology. As illustrated in FIG. 1, a blood coagulation system analysis apparatus 100 according to the present technology includes an estimating unit 101. The blood coagulation system analysis apparatus 100 according to the present technology may further include other components. Examples of components that can be included in the blood coagulation system analysis apparatus according to the present technology can include a sample holding unit 102, a measuring unit 103, a result calculating unit 104, a comparing unit 105, and a display unit 106. In addition, the blood loss prediction apparatus according to the present technology may include a storage unit (not illustrated), if necessary. Hereinafter, the estimating unit 101 will be first described.

In the present technology, the estimating unit estimates a characteristic regarding the inhibitor on the basis of the comparison result between the first result and the second result. The estimating unit shows an effect that the characteristic regarding the inhibitor is estimated.

(1) Blood Coagulation Factor and Inhibitor of Blood Coagulation Factor

In the present technology, the blood coagulation factor is, for example, an extrinsic coagulation factor or an intrinsic coagulation factor, or may be a coagulation system activator. In the present technology, it is preferable that the blood coagulation factor is the extrinsic coagulation factor. Examples of the extrinsic coagulation factor can include factor III (tissue factor), factor VII and activated forms thereof, that is, activated factor VII, and recombinant forms thereof. Examples of the intrinsic coagulation factor can include factor VIII, factor IX, factor XI, and factor XII, and activated forms thereof, for example, activated factor VIII or the like, and genetically modified forms thereof. Examples of the coagulation system activator can include ellagic acid and kaolin. Ellagic acid and kaolin can activate an intrinsic coagulation pathway. In the present technology, it is particularly preferable that the blood coagulation factor is factor III, that is, a tissue factor. In the present technology, in a case where the blood coagulation factor is the tissue factor, better estimation (or prediction in a case of a blood loss prediction apparatus described in the following 2.) can be performed.

In the present technology, the inhibitor of the blood coagulation factor can be, for example, an inhibitor of the extrinsic coagulation factor or the intrinsic coagulation factor, and can be particularly an inhibitor of the coagulation factor described above (for example, the tissue factor or the like). Examples of the inhibitor can include, but are not limited to, TFPI, antithrombin, protein C, and protein S. In the present technology, it is particularly preferable that the inhibitor is TFPI. In the present technology, in a case where the inhibitor is TFPI, better estimation (or prediction in a case of a blood loss prediction apparatus described in the following 2.) can be performed.

In the present technology, the blood is particularly animal blood, more preferably mammalian blood, even more preferably primate blood, and even more preferably human blood. In the present technology, the blood may be whole blood. In the present technology, since estimation (or prediction in a case of a blood loss prediction apparatus described in the following 2.) can be performed using the whole blood, there is also an advantage that separation of blood components is not required.

Hereinafter, a coagulation reaction system will be described in detail. The coagulation reaction system is divided into on a mechanism (extrinsic system) triggered by formation of a complex of tissue factor (TF) and activated coagulation Factor VII and a mechanism (intrinsic system) triggered by activation of Factor XII due to a cause such as contact with a foreign substance, and these mechanisms are joined to each other at a stage of activating Factor X. It should be noted that in accordance with the practice in thrombosis and hemostasis fields, each coagulation factor will hereinafter be represented by placing "F" before the Roman numeral as its factor number and that in a case where it has been activated, "a" will hereinafter be added to the end. For example, factor XII and activated factor VII are represented as FXII and FVIIa, respectively. Formed FXa activates prothrombin (FII) to convert prothrombin (FII) to thrombin (FIIa), and fibrinogen is converted into fibrin by an action of thrombin. Formed fibrin molecules polymerize with each other to form hardly-soluble polymer fibers, and further form a three-dimensional network structure called stabilized fibrin by an action of FXIIIa or blood platelets. A structure in which red blood cells are mainly involved in this network structure is a thrombus. Once the thrombus is formed, a fibrinolytic reaction system begins to work in order to prevent coagulation from excessively progressing, such that the thrombus that has completed a role of hemostasis will be dissolved in due time.

In an actual living body, life is maintained by an exquisite mechanism in which blood coagulation occurs simultaneously with aggregation of blood platelets at a part requiring hemostasis due to vascular injury or the like, and at the same time, fluidity of blood is maintained at the other parts to keep a blood flow to the periphery, in an actual living body. To that end, a mechanism that regulates and controls the coagulation system or the fibrinolysis system described above plays a large role. Conversely, when these mechanisms fail, a serious result such as defective hemostasis or thrombosis may be caused. It is known that TFPI, antithrombin, and a protein C/S system are central molecules in a regulating mechanism of a blood coagulation system. These control factors effectively show functions by their relationships with vascular endothelial cells. For example, TFPI exist in a state of binding to heparan sulfate, and the like on the vascular endothelial cells to inhibit a TF/FVIIa complex, thereby suppressing an extrinsic coagulation pathway. In particular, this inhibition activity is remarkably enhanced by binding FXa to a specific part of TFPI. That is, even in a case where a blood coagulation reaction progresses at a bleeding site, such that excessive FXa is produced, a feedback mechanism that suppresses excessive thrombogenesis is activated via TFPI in a remote healthy blood vessel part.

(2) Electrical Characteristic

In the present technology, examples of the electrical characteristic can include a permittivity, an impedance, an admittance, a capacitance, a conductance, a conductivity, a phase angle, and the like. In the present technology, the electrical characteristic may be any one or more than two of the permittivity, the impedance, the admittance, the capacitance, the conductance, the conductivity, and the phase angle. These electrical characteristics are mutually convertible by Equations shown in the following Table 1. Most of these electric amounts or physical property values can be represented using complex numbers, such that Conversion Equations can be simplified. The electrical characteristic used in the present technology may preferably be a permittivity. For example, a complex impedance is measured as the electrical characteristic, and the permittivity can be determined on the basis of the complex impedance.

TABLE 1

<Main electric amount and physical property values that are mutually convertible>

| Electric amount and physical property value | Sign | In case where electric amount and physical property value are represented by complex number |
|---|---|---|
| Voltage | V | $V^* = \|V\| \exp j(\omega t + \varphi)$ |
| Current | I | $I^* = \|I\| \exp j(\omega t + \varphi)$ |
| Impedance | Z | $Z^* = R + jX$ (R: resistance, X: reactance) |
| Admittance | Y | $Y^* = G + jB$ (G: conductance, B: susceptance) |
| Capacitance | C | $C^* = C - jG/\omega$ |
| Conductance | G | $G^* = G + j\omega C$ |
| Loss tangent (Dielectric tangent) | D or tan δ | |
| Loss angle | δ | |
| Phase angle | θ | |
| Q-value | Q | |
| Permittivity | ε | $\varepsilon^* = \varepsilon - j\kappa/\omega\varepsilon_0$ |
| Conductivity | κ | $\kappa^* = \kappa + j\omega\varepsilon_0\varepsilon$ |

<Equations in which respective electric amounts and physical property values are associated with each other>

$$Z^* = V^*/I^*$$

$$\theta = \phi - \varphi$$

$$Y^* = 1/z^*$$

$$C = B/\omega$$

$$D = \tan \delta = G/\omega C = 1/Q$$

$$\varepsilon^* = C^*/C_0$$

$$\kappa^* = j\omega\varepsilon_0\varepsilon^*$$

ω: angular frequency
$\varepsilon_0$: permittivity in vacuum (constant)
$C_0$: constant depending on measurement apparatus
Value to which * is attached: complex number In the present technology, the measured electrical characteristics can be standardized, if necessary. The standardization can be performed using, for example, an initial value measured immediately after measurement starts or a minimum value or a maximum value of the permittivity.

In the present technology, the electrical characteristic can be any electrical characteristic obtained by applying a voltage having an arbitrary frequency, particularly an alternating voltage to the blood. Preferably, the frequency of the alternating voltage can be 1 kHz to 50 MHz, more preferably 3 kHz to 30 MHz, more preferably 0.1 MHz to 20 MHz, more preferably 0.5 MHz to 15 MHz, and even more preferably 1 MHz to 10 MHz. By using these frequencies, it is possible to obtain electrical characteristics more suitable for estimation (or prediction in a case of a blood loss prediction apparatus described in the following 2.) in the present technology.

Measurement of the electrical characteristics can be performed by apparatuses described in Japanese Patent Application Laid-Open No. 2010-181400 or Japanese Patent Application Laid-Open No. 2012-194087. A specific method of the measurement can also be performed according to methods described in these documents.

(3) First Result and Second Result

In the present technology, the first result regarding the blood coagulation inhibition ability of the inhibitor can be obtained on the basis of the electrical characteristic. The first result can be, for example, a rate of change of the electrical characteristic or an integral value of the electrical characteristic, preferably a rate of change of the electrical characteristic. The first result can be, more preferably, a rate of change of the electrical characteristic at a point in time when a change over time in the electrical characteristic becomes maximum after blood coagulation starts or an average value of rates of change of a certain period before and after the point in time. An anticoagulant effect is removed by adding an anticoagulant effect removing agent (for example, a calcium-containing compound, particularly calcium chloride, or the like) to the blood whose coagulation is suppressed by an anticoagulant (for example, citric acid or the like), and coagulation of the blood then starts. In a case where the electrical characteristic of the blood is measured over time, there is a point in time when a change over time in the electrical characteristic becomes maximum after the coagulation of the blood starts. A rate of change of the electrical characteristic at the point in time can be the first result in the present technology.

Hereinafter, the first result will be described in more detail with reference to FIG. 2.

Figure 2:
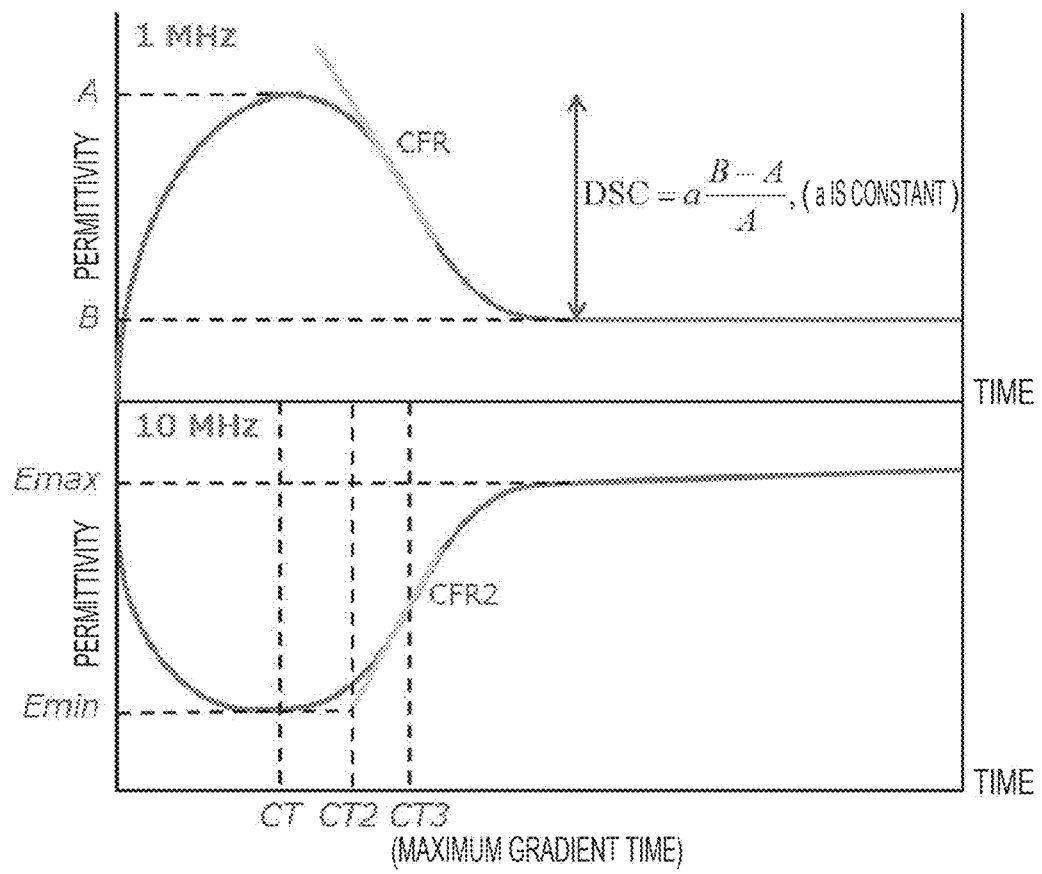
FIG. 2 is a diagram illustrating an example of a plot of permittivity with respect to time.

FIG. 2 is an example of a plot of permittivity with respect to time, the permittivity being measured with respect to the blood in a case where an alternating voltage having a predetermined frequency is applied to the blood in a coagulation process. A left end of a time axis in FIG. 2 is a point in time when an anticoagulant effect removing agent is added.

In a case where the frequency of the voltage is 10 MHz, after the anticoagulant effect removing agent is added, the permittivity is decreased to arrive at a minimum value $E_{min}$, and is then increased. A point in time of the minimum value $E_{min}$ is at a point in time (CT in FIG. 2) when the coagulation starts. After the coagulation starts, a change (increase rate) overtime in the permittivity becomes maximum at a point time of CT3 in FIG. 2. A gradient of a curve (CFR2 in FIG. 2) representing a change in the permittivity with respect to time at this point in time, that is, a rate of change of the permittivity with respect to time can be the first result in the present technology.

In addition, in a case where the frequency of the voltage is 1 MHz, after the anticoagulant effect removing agent is added, the permittivity is increased to arrive at a maximum value A, and is then decreased. A point in time of the maximum value A is at a point in time (CT in FIG. 2) when the coagulation starts. After the coagulation starts, even in a case where the frequency of the voltage is 1 MHz, there is a point in time when a change (decrease rate) over time in the permittivity becomes maximum. A gradient of a curve (CFR in FIG. 2) representing a change in the permittivity with respect to time at this point in time, that is, a rate of change of the permittivity with respect to time can be the first result in the present technology.

In the present technology, the second result regarding the blood coagulation inhibition ability of the inhibitor is obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added. That is, a concentration of the blood coagulation factor in a blood sample used to obtain the second result is different than that of the blood coagulation factor in a blood sample used to obtain the first result.

A difference between the concentration of the blood coagulation factor in the blood from which the first result is obtained and the concentration of the blood coagulation factor in the blood from which the second result is obtained is preferably 0.25 pM or more, and more preferably is 0.30 pM or more, and a better estimation result (or prediction result in a case of a blood loss prediction apparatus described in the following 2.) can be obtained by setting the difference between the concentrations in two bloods whose electrical characteristics are measured as described above.

The difference is particularly preferably 0.50 pM or more, even more preferably 0.52 pM or more, even more preferably 0.55 pM or more, and even more preferably 0.57 pM or more. By setting the difference between the concentrations in the two bloods whose electrical characteristics are measured as described above, a better estimation result (or prediction result in a case of a blood loss prediction apparatus described in the following 2.) can be obtained as compared with, for example, a case where the difference between the concentrations is about 0.3 pM. The concentration of the blood coagulation factor is calculated on the basis of only an amount of blood coagulation factor added to the blood. That is, an amount of blood coagulation factor originally contained in the blood is not taken into account in the calculation of the concentration. For example, in a case where the blood used to obtain the second result is blood to which the blood coagulation factor is not added, the concentration of the blood coagulation factor is zero.

In a case where the blood coagulation factor is added to both of the blood from which the first result is obtained and the blood from which the second result is obtained, the concentration of the blood coagulation factor in the blood from which the first result is obtained can be preferably 1.9 times or more, and more preferably 1.95 times or more the concentration of the blood coagulation factor in the blood from which the second result is obtained. By setting the concentrations as described above, a better estimation result (or prediction result in a case of a blood loss prediction apparatus described in the following 2.) can be obtained.

The concentration of the blood coagulation factor in the blood from which the first result is obtained can be particularly preferably 5 times or more, and even more preferably 6 times or more, 7 times or more, or 8 times or more the concentration of the blood coagulation factor in the blood from which the second result is obtained. By setting the concentration as described above, a better estimation result (or prediction result in a case of a blood loss prediction apparatus described in the following 2.) can be obtained as compared with a case where the difference between the concentrations is about twice.

In the present technology, both of the concentration of the blood coagulation factor in the blood from which the first result is obtained and the concentration of the blood coagulation factor in the blood from which the second result is obtained can be preferably 20 pM or less, more preferably 15 pM or less, more preferably 7 pM or less, more preferably 5 pM or less, and even more preferably 3 pM or less. By setting the concentrations of the blood coagulation factors to these concentrations or less, the electrical characteristics can be more accurately measured.

The electrical characteristic used to obtain the second result can be measured by the same method as a method of measuring the electrical characteristic used to obtain the first result. The second result can be obtained on the basis of the electrical characteristic by the same method as a method of obtaining the first result. That is, as described above, the second result can be preferably the rate of change of the electrical characteristic, and more preferably the rate of change of the electrical characteristic at the point in time when the change over time in the electrical characteristic becomes maximum after the blood coagulation starts.

(4) Comparison Result Between First Result and Second Result

In the present technology, the comparison result between the first result and the second result can be preferably a ratio between the first result and the second result or a result obtained by correcting the ratio by a predetermined correction term. By performing the estimation using the ratio or the result obtained by correcting the ratio by the predetermined correction term, a better estimation result (or prediction result in a case of a blood loss prediction apparatus described in the following 2.) can be obtained.

In the present technology, for example, in a case where the blood coagulation factor is the extrinsic coagulation factor, the first result and the second result are represented as f (EX1α) and g (EX2α), respectively, and the ratio is represented as y. The relationship between the first and second results and the ratio can be represented by the following Equation 1.

[Equation 1]

$$y=f(EX1\alpha)/g(EX2\alpha) \qquad \text{Equation 1}$$

In Equation 1, functions f and g can be, for example, higher-order functions or irrational functions. In addition, concentration of TFPI=EX1α$^m$/EX2α$^n$ or m=n=1. These are merely examples, and the present technology is not limited thereto.

In the present technology, in a case where the coagulation factor is, for example, the tissue factor, a better evaluation of TFPI is possible by the above comparison. One of the reasons why such a better evaluation is possible is that an assay in which a concentration of the tissue factor is low is more strongly subjected to an inhibition effect caused by TFPI than an assay in which a concentration of the tissue factor is high, but a difference between influences by TFPI in both assays is small.

In the present technology, the above Equation 1 may be further corrected. For example, the correction can be further performed on the above Equation 1 by a hematocrit value of the blood sample. The Equation on which the correction is performed can be the following Equation 2.

[Equation 2]

$$y=f(EX1\alpha)/g(EX2\alpha)*h(Hct) \qquad \text{Equation 2}$$

In Equation 2, h (Hct) is a function regarding the hematocrit value of the blood sample. Hct can be a hematocrit value of a specimen or a value (measured value or calculated value) directly convertible into the hematocrit value. For example, h (Hct)=100%−Hct value (%).

By the above correction, a better estimation result (or prediction result in a case of a blood loss prediction apparatus described in the following 2.) can be obtained. In the present technology, in a case of measuring the electrical characteristic such as the permittivity of the blood, a concentration of the added blood coagulation factor in plasma is affected by a difference in an excluded volume effect due to red blood cells. For example, in a specimen having a high hematocrit value, an effective concentration of the blood coagulation factor in the plasma can be high. Therefore, this influence can be reduced by performing the above correction.

The hematocrit value may be measured by a blood count apparatus or the like used in the related art, or may be calculated on the basis of the electrical characteristic. A method of calculating the hematocrit value on the basis of the electrical characteristic is described in, for example, International Publication No. WO 2014/141844. In a case of using the hematocrit value calculated on the basis of the electrical characteristic, it is possible to calculate the hematocrit value together with the measurement of the electrical characteristics for obtaining the first result and the second result, such that there is no need to separately measure the hematocrit value using the blood count apparatus or the like.

In the present technology, the above Equation 2 may be further corrected. For example, the above Equation 2 can further be corrected by a characteristic value regarding an intrinsic coagulation pathway. The Equation on which the correction is performed can be the following Equation 3.

[Equation 3]

$$y=f(EX1\alpha)/g(EX2\alpha)*h(Hct)*I(s) \qquad \text{Equation 3}$$

In Equation 3, I (s) can be a correction function regarding the intrinsic coagulation pathway, and s can be a parameter obtained in an assay regarding the intrinsic coagulation factor or a calculation result using a plurality of parameters obtained in the assay regarding the intrinsic coagulation factor.

In the blood coagulation reaction, FXIIa, the intrinsic coagulation factor, has an ability not only to activate the intrinsic system but also activate extrinsic coagulation factor FVII. In addition, a TF/FVIIa complex has an ability not only to activate FX but also activate intrinsic coagulation factor FIX. The activated FIXa activates FX to contribute to thrombin formation, which further leads to activation of FVII (that is, promotion of an extrinsic coagulation reaction). In this way, the extrinsic coagulation pathway and the intrinsic coagulation pathway interact with each other. For this reason, in a case where there are two specimens whose concentrations of the extrinsic coagulation factors and concentrations of TFPIs are exactly the same as each other, but a concentration of an intrinsic coagulation factor of one of the two specimens is significantly higher than that of the other, coagulation reactions of the two specimens may be different from each other. For this reason, a better estimation result can be obtained by the correction by the characteristic value regarding the intrinsic coagulation pathway.

In the present technology, in the above Equation 3, a plurality of results may be used as the first and second results regarding the extrinsic coagulation factor, respectively. In this case, the comparison result y can be represented, for example, as follows.

[Equation 4]

$$y=F(p)*G(r)*h(Hct)*I(s) \qquad \text{Equation 4}$$

In Equation 4, p is a calculation result using a plurality of parameters obtained in an assay regarding the extrinsic coagulation factor, and F (p) is a function of p. r is a calculation result using the plurality of parameters obtained in the assay with respect to blood having a concentration of a blood coagulation factor different from that of a blood coagulation factor added to blood in which the result regarding p was obtained, and G(r) is a function of r. Examples of the plurality of parameters can include the rate of change of the electrical characteristic described above and DSC as illustrated in FIG. 1. By using the plurality of parameters, a better estimation result (or prediction result in a case of a blood loss prediction apparatus described in the following 2.) can be obtained.

In the present technology, preferably, for example, both of f(EX1α) and g(EX2α) in the above Equation 1 can be rates of change of the electrical characteristics at the point in time when the change over time in the electrical characteristic becomes maximum after the blood coagulation starts. That is, the above Equation 1 is represented as follows.

[Equation 5]

$$y = CFR2_{EX1}/CFR2_{EX2} \quad \text{Equation 5}$$

In Equation 5, $CFR2_{EX1}$ is a rate of change of the electrical characteristic at the point in time when the change over time in the electrical characteristic becomes maximum after the blood coagulation starts, and is the first result. $CFR2_{EX2}$ is also a rate of change of the electrical characteristic at the point in time when the change overtime in the electrical characteristic becomes maximum after the blood coagulation starts, and is the second result. However, as described above, the concentration of the blood coagulation factor in the blood used to obtain the first result is different from that of the blood coagulation factor in the blood used to obtain the second result. In the present technology, by using y in Equation 5 as the comparison result, a better estimation result (or prediction result in a case of a blood loss prediction apparatus described in the following 2.) can be obtained.

In the present technology, preferably, for example, both of f(EX1α) and g(EX2α) in the above Equation 2 can be rates of change of the electrical characteristics at the point in time when the change over time in the electrical characteristic becomes maximum after the blood coagulation starts, and h(Hct) can be 100%−Hct value (%). That is, the above Equation 2 is represented by the following Equation 6. It should be noted that in Equation 6, $CFR2_{EX1}$ and $CFR2_{EX2}$ are as described in the above Equation 5. In the present technology, by using y in Equation 6 as the comparison result, a better estimation result (or prediction result in a case of a blood loss prediction apparatus described in the following 2.) can be obtained.

[Equation 6]

$$y = \frac{CFR2_{EX1}(100 - Hct)}{CFR2_{EX2}} \quad \text{Equation 6}$$

In the present technology, the characteristic regarding the inhibitor can be, for example, a concentration or an activity of the inhibitor. That is, in the present technology, for example, the concentration or activity of the inhibitor can be quickly estimated on the basis of a measured value of the electrical characteristic without being actually measured by a chemical or biochemical method.

(5) Estimation of Characteristic Regarding Inhibitor

In the present technology, the estimating unit estimates the characteristic regarding the inhibitor of the blood coagulation factor on the basis of the comparison result. The estimation can be performed on the basis of, for example, a correlation between the comparison result and the characteristic. The correlation can be prepared in advance, for example, as follows. Electrical characteristics are measured for blood samples obtained, respectively, from a plurality of individuals, particularly persons, and a comparison result between the first result and the second result is obtained on the basis of a measurement result. Characteristics regarding inhibitors, for example, concentrations or activities of the inhibitors, or the like, are actually measured for the blood samples of the plurality of individuals by a chemical or biochemical method. A correlation between the comparison result and the characteristics regarding the inhibitors is obtained by statistical processing. Similarly, a comparison result is also obtained for blood of an individual whose characteristic regarding an inhibitor is to be estimated, and the characteristic regarding the inhibitor can be estimated on the basis of the comparison result with reference to the correlation, for example, a graph or an equation representing the correlation, or the like. The comparison result may be the ratio between the first result and the second result as described above, and can be particularly y represented by any of the above Equations 1 to 6.

In the present technology, the characteristic of the inhibitor is estimated as described above, such that the characteristic can be known without being actually measured by a time-consuming chemical or biochemical method, in a case of wanting to know the characteristic of the inhibitor as quickly as possible, for example, in a case of a perioperative period, in a case of emergency lifesaving, or the like. As a result, for example, blood transfusion or hemostasis treatment can be performed on the basis of evidence, such that protraction of bleeding can be prevented and the prognosis of treatment can be improved. In addition, a treatment necessary for hemostasis is early performed, such that a frequency of re-hemostasis treatment is decreased to realize a reduction in a medical cost.

The chemical or biochemical measurement of the characteristic regarding the inhibitor performed in order to obtain the correlation may be performed by a method generally used in the related art. For example, in a case where the characteristic is a concentration, the concentration can be measured using, for example, an EIA, particularly, an ELISA, or an RIA. For example, in a case where the characteristic is a concentration of TFPI, the concentration of TFPI can be measured by the ELISA. In a case where the characteristic is an activity, the activity can be measured by evaluating an inhibition action of an inhibitor whose activity is to be measured performs inhibition by using a substrate of an activated form of a factor activated in a pathway inhibited by the inhibitor or a factor activated in a downstream of the pathway. For example, in a case where the characteristic is an activity of TFPI, the activity can be measured by a method of measuring an inhibition action against an activation reaction of factor X caused by a TF/VIIa complex by using a synthetic substrate of factor Xa. In the present technology, for example, the concentration of TFPI of the blood sample can be estimated on the basis of a measured value of the electrical characteristic with reference to the previously obtained correlation between the comparison result and the concentration of TFPI.

The estimating unit may further estimate an amount of drug to be administered or a time required for stabilization, on the basis of the estimation result, if necessary. Appropriate treatment depending on the characteristic of the blood can be performed by estimating the amount of drug or the time.

The estimation can be performed by introducing the estimating unit into an electrical characteristic measurement apparatus according to the related art (for example, an apparatus described in Japanese Patent Application Laid-Open No. 2010-181400 or Japanese Patent Application Laid-Open No. 2012-194087, or the like). For this reason, a cost required for introducing a new equipment is reduced, and a space in which the apparatus is installed is saved. In addition, labor can be reduced in a clinical field.

(6) Other Components

The blood coagulation system analysis apparatus according to the present technology may include a component that is used to acquire various data used for the estimation performed in the estimating unit, a component that outputs the estimated characteristic, and/or a component that stores the various data, if necessary. Examples of such components can include a sample holding unit 102 that holds a blood sample, a measuring unit 103 that measures an electrical characteristic, a result calculating unit 104 that obtains results regarding a blood coagulation inhibition ability of an inhibitor, a comparing unit 105 that compares a first result and a second result with each other, a display unit 106 that displays the estimated characteristic, and a storage unit (not illustrated), as illustrated in FIG. 1, but are not limited thereto. Hereinafter, each of these components will be described.

In the present technology, the sample holding unit 102 holds the blood sample. The blood sample can be held in the sample holding unit 102 in a state where it contains an anticoagulant such as citric acid. The sample holding unit 102 can automatically warm the blood sample to about 37° C. when the blood sample is put in the sample holding unit 102. In addition, the sample holding unit 102 can have a pipetting mechanism. The blood is appropriately stirred by the pipetting mechanism, and as a result, blood sedimentation can be eliminated. For example, the pipetting mechanism can detect a liquid level of the blood by a mechanism that automatically detects the liquid level of the blood, suck the blood at a predetermined depth from the detected liquid level, and discharge the blood at a predetermined height from the deepest part of the blood. The stirring by the pipetting mechanism can be performed as described in, for example, Japanese Patent Application Laid-Open No. 2016-045071.

In the present technology, the measuring unit 103 measures the electrical characteristic of the blood sample. The electrical characteristic and a method of measuring the electrical characteristic are as described above. The measuring unit 103 may be provided with, for example, a cartridge in which a blood coagulation factor and an anticoagulant effect removing agent for removing an anticoagulant effect are preliminarily put. The blood is injected from the sample holding unit 102 to the cartridge, and is then mixed with the blood coagulation factor and the anticoagulant effect removing agent. As a result of the mixing, a blood coagulation process starts. Then, in the measuring unit 103, the electrical characteristic of the blood in the blood coagulation process can be measured as described above. Alternatively, two or more cartridges may be provided in the measuring unit 103. Electrical characteristics of blood in the two or more cartridges may be simultaneously measured. For example, the two cartridges each contain different amounts of blood coagulation factors, such that it is possible to simultaneously measure an electrical characteristic for obtaining the first result and an electrical characteristic for obtaining the second result. Alternatively, voltages having different frequencies may be applied to a plurality of cartridges, respectively, to measure electrical characteristics in the respective cartridges. The electrical characteristics measured in this manner can be used to calculate the first and second results in the result calculating unit 104.

In the present technology, the result calculating unit 104 obtains the results regarding the blood coagulation inhibition ability of the inhibitor on the basis of the electrical characteristic. The results and a method of calculating the results are as described above. The results can be used for the comparison in the comparing unit 105.

In the present technology, the comparing unit 105 compares the first result and the second result with each other. A method of comparing the first result and the second result with each other is as described above. The estimating unit 101 can estimate the characteristic regarding the inhibitor on the basis of a comparison result.

In the present technology, the display unit 106 displays the characteristic estimated by the estimating unit 101. In addition, the display unit 106 may display the electrical characteristic, the first result and the second result, and/or the comparison result, if necessary.

In addition, the blood coagulation system analysis apparatus according to the present technology may include a storage unit (not illustrated), if necessary. The storage unit can store the estimation result, and can store one or more data selected from a correlation used to obtain the estimation result, the first and second results, the electrical characteristic, and an amount of added coagulation factor, if necessary. In addition, the storage unit may store information regarding the blood sample. The information may be input through, for example, an user interface of the blood coagulation system analysis apparatus, or may be input by reading a barcode or the like. Examples of the information regarding the blood sample can include a type of electrical characteristic to be measured, types of first and second results to be determined, a type of blood coagulation factor to be added, a type of inhibitor whose characteristic is to be determined, a type of characteristic to be estimated, a method of comparing the first and second results with each other, an equation used to obtain a comparison result, and a correlation or the like, used for estimation, but are not limited thereto. Each of the above units can be operated on the basis of these pieces of information.

2. Blood Loss Prediction Apparatus

A blood loss prediction apparatus according to the present technology includes: a predicting unit that predicts a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

Figure 3:
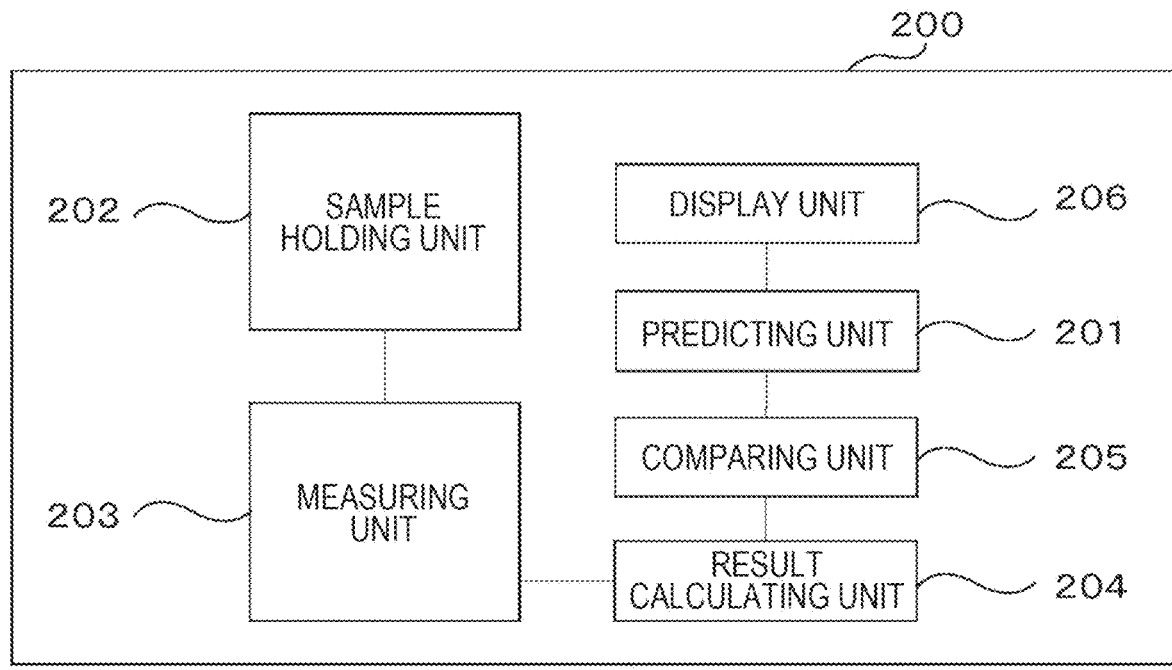
FIG. 3 is a schematic diagram illustrating a configuration of a blood loss prediction apparatus.

FIG. 3 schematically illustrates a configuration of a blood loss prediction apparatus according to the present technology. As illustrated in FIG. 3, a blood loss prediction apparatus 200 according to the present technology includes a predicting unit 201. The blood coagulation system analysis apparatus 200 according to the present technology may further include other configurations. Examples of components that can be included in the blood coagulation system analysis apparatus according to the present technology can include a sample holding unit 202, a measuring unit 203, a result calculating unit 204, a comparing unit 205, and a display unit 206. In addition, the blood loss prediction apparatus according to the present technology may include a storage unit (not illustrated), if necessary. Components other than the predicting unit 201 among these components are the same as those described with respect to the blood coagulation system analysis apparatus in the above 1., and a description thereof is thus omitted. Hereinafter, the predicting unit 201 will be described.

In the present technology, the predicting unit predicts the blood loss of the individual on the basis of the comparison result between the first result and the second result. The predicting unit shows an effect that the blood loss of the individual is predicted.

All of the descriptions regarding the blood coagulation system analysis apparatus according to the present technology in the above 1. (1) to (4) are also applied to the blood loss prediction apparatus according to the present technology. That is, all of the descriptions regarding the comparison result used for the estimation in the estimating unit of the blood coagulation system analysis apparatus according to the present technology and matters for obtaining the comparison result are also applied to the comparison result used for the prediction in the predicting unit of the blood loss prediction and matters for obtaining the comparison result. For this reason, with respect to the predicting unit, descriptions of the blood coagulation factor and the inhibitor of the blood coagulation factor, the electrical characteristic, the first result and the second result, and the comparison result between the first result and the second result are omitted. Hereinafter, prediction of the blood loss of the individual will be described.

In the present technology, the predicting unit predicts the blood loss of the individual on the basis of the comparison result between the first result and the second result. The prediction can be performed on the basis of, for example, a correlation between the comparison result and the blood loss. The correlation can be prepared in advance, for example, as follows. Electrical characteristics are measured for blood samples obtained, respectively, from a plurality of individuals who underwent specific surgery, particularly persons, and a comparison result between the first result and the second result is obtained on the basis of a measurement result. Meanwhile, blood losses after the surgery are measured from the plurality of individuals. For example, in a case of cardiovascular surgery, a blood loss after closing the chest can be measured. The correlation between the comparison result and the blood loss is obtained by statistical processing. The comparison result is also obtained for blood of an individual whose blood loss is to be predicted, and the blood loss can be predicted on the basis of the comparison result with reference to the correlation, for example, a graph or an equation representing the correlation, or the like. The comparison result may be the ratio between the first result and the second result as described above, and can be particularly y represented by any of the above Equations 1 to 6. More preferably, the comparison result can be represented by Equation 6. A more preferable prediction result can be obtained by using Equation 6.

In the blood loss prediction apparatus according to the present technology, the blood loss can be, for example, a blood loss after surgery or a blood loss due to injury with bleeding. The surgery may be particularly a surgery for performing treatment for adding the coagulation inhibitor to the blood.

In the present technology, the individual is preferably an animal, more preferably a mammal, even more preferably a primate, and even more preferably a person.

In the present technology, the blood loss is predicted, such that, for example, in a case of a perioperative period, in a case of emergency lifesaving, or the like, for example, blood transfusion or hemostasis treatment can be performed on the basis of evidence. Therefore, protraction of bleeding can be prevented and prognosis of the treatment can be improved. For example, according to the present technology, the blood loss after the surgery or after the injury can be predicted, which can be useful for determination of an amount of blood transfusion or a dosage requiring a prediction result of the blood loss. In addition, in a case where it is predicted that the blood loss will be increased, a treatment necessary for hemostasis is early performed, such that a frequency of re-hemostasis treatment can be decreased to realize a reduction in a medical cost.

The prediction can be performed by introducing the predicting unit into the electrical characteristic measurement apparatus according to the related art (for example, an apparatus described in Japanese Patent Application Laid-Open No. 2010-181400 or Japanese Patent Application Laid-Open No. 2012-194087, or the like). For this reason, a cost required for introducing a new equipment is reduced, and a space in which the apparatus is installed is saved. In addition, labor can be reduced in a clinical field.

3. Blood Coagulation System Analysis System

The present technology also provides a blood coagulation system analysis system including a blood coagulation system analysis apparatus and a display apparatus that displays an estimation result by the blood coagulation system analysis apparatus. The blood coagulation system analysis apparatus is the blood coagulation system analysis apparatus described in the above 1.

The blood coagulation system analysis system according to the present technology includes the display apparatus that displays the estimation result. The display apparatus may display one or more data selected from a correlation used to obtain the estimation result, the first and second results, the electrical characteristic, and an amount of added coagulation factor, in addition to the estimation result.

The blood coagulation system analysis system according to the present technology may further include a server and/or a user interface. The server can include a storage unit that stores the estimation result, and stores one or more data selected from the correlation used to obtain the estimation result, the first and second results, the electrical characteristic, and the amount of added coagulation factor, if necessary. The interface can be a unit for a user to operate the blood coagulation system analysis system or the blood coagulation system analysis apparatus. The user can perform an operation for blood coagulation system analysis or can display an analysis result through the interface.

The blood coagulation system analysis system according to the present technology can further includes components used to acquire various data used for the estimation performed in the estimating unit described in the above 1., for example, the sample holding unit, the measuring unit, the result calculating unit, the comparing unit, and the like. The respective units and the display apparatus included in the blood coagulation system analysis system according to the present technology may be connected to each other through a network.

Figure 4:
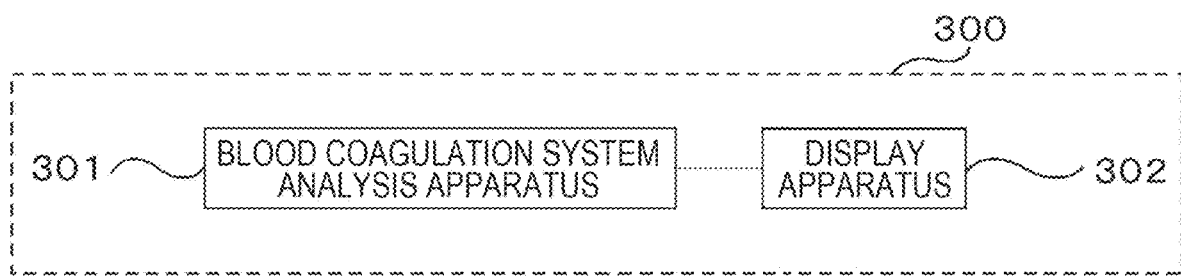
FIG. 4 is a schematic diagram illustrating a configuration of a blood coagulation system analysis system.

FIG. 4 schematically illustrates a configuration of a blood coagulation system analysis system according to the present technology. As illustrated in FIG. 4, a blood coagulation system analysis system 300 according to the present technology includes a blood coagulation system analysis apparatus 301 and a display apparatus 302.

4. Blood Loss Prediction System

The present technology provides a blood loss prediction system including a blood loss prediction apparatus. The blood loss prediction apparatus is the blood loss prediction apparatus described in the above 2.

The blood loss prediction system according to the present technology includes a display apparatus that displays a prediction result predicted by the blood loss prediction apparatus. The display apparatus may display one or more data selected from a correlation used to obtain the prediction result, the first and second results, the electrical characteristic, and an amount of added coagulation factor, in addition to the prediction result.

The blood loss prediction system according to the present technology may further include a server and/or a user interface. The server can include a storage unit that stores the prediction result, and stores one or more data selected from a correlation used to obtain the prediction result, the first and second results, the electrical characteristic, and an amount of added coagulation factor, if necessary. The interface can be a unit for a user to operate the blood loss prediction system or the blood loss prediction apparatus. The user can perform an operation for blood loss prediction or can display a blood loss prediction result through the interface.

The blood loss prediction system according to the present technology can further includes components used to acquire various data used for the prediction performed in the predicting unit described in the above 2., for example, the sample holding unit, the measuring unit, the result calculating unit, the comparing unit, and the like. The respective units or the display apparatus included in the blood loss prediction system according to the present technology may be connected to each other through a network.

Figure 5:
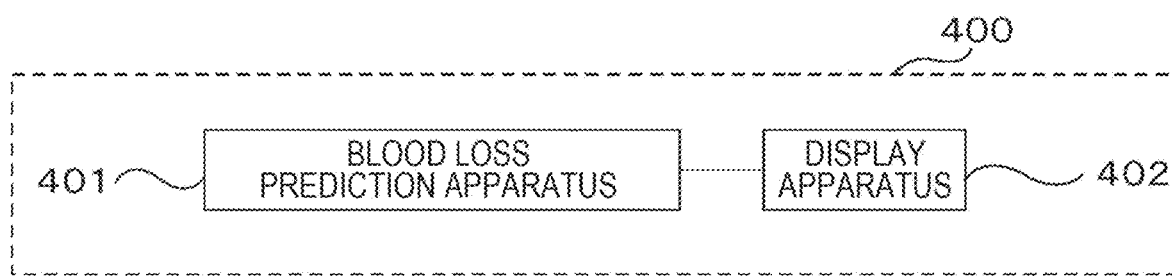
FIG. 5 is a schematic diagram illustrating a configuration of a blood loss prediction system.

FIG. 5 schematically illustrates a configuration of a blood loss prediction system according to the present technology. As illustrated in FIG. 5, a blood loss prediction system 400 according to the present technology includes a blood loss prediction apparatus 401 and a display apparatus 402.

5. Blood Coagulation System Analysis Method

The present technology also provides a blood coagulation system analysis method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of estimating a characteristic regarding the inhibitor on the basis of a comparison result.

In the step of the comparing, the first result and the second result are compared with each other. The comparison result in the step of the comparing is used for the estimation in the step of the estimating. All of the descriptions regarding the blood coagulation system analysis apparatus according to the present technology in the above 1. (1) to (4) are applied to the step of the comparing in the blood coagulation system analysis method according to the present technology. That is, the descriptions of the blood coagulation factor and the inhibitor of the blood coagulation factor, the electrical characteristic, the first result and the second result, and the comparison result between the first result and the second result mentioned with respect to the blood coagulation system analysis apparatus according to the present technology are also applied to the step of the comparing. For this reason, these descriptions are omitted.

In the step of the estimating, the characteristic regarding the inhibitor is estimated on the basis of the comparison result. All of the descriptions regarding the blood coagulation system analysis apparatus according to the present technology in the above 1. (4) and (5) are applied to the step of the estimating in the blood coagulation system analysis method according to the present technology. That is, all of the descriptions of the comparison result mentioned with respect to the blood coagulation system analysis apparatus according to the present technology and the estimation based on the comparison result are also applied to the step of the estimating. For this reason, these descriptions are omitted.

The blood coagulation system analysis method according to the present technology may further include a step of acquiring various data used in the step of the comparing and the step of the estimating, if necessary. An example of such a step can include a step of adding the blood coagulation factor to the blood, a step of measuring an electrical characteristic of a blood sample, and a step of calculating a result regarding the blood coagulation inhibition ability of the inhibitor, but is not limited thereto. In these steps, the respective methods executed in the sample holding unit, the measuring unit, and the result calculating unit described in the above 1. can be performed.

An embodiment of the blood coagulation system analysis method according to the present technology will be described with reference to a flowchart described in FIG. 6.

In a blood coagulation factor adding step (S501), the blood coagulation factor is added to blood samples. The same blood samples are mixed with the blood coagulation factor at two concentrations, such that two blood samples having coagulation factor at different concentrations are prepared. The blood coagulation factor adding step (S501) can be performed by the measuring unit described in 1. (6), particularly the cartridge included in the measuring unit.

In an electrical characteristic measuring step (S502), electrical characteristics of each of the blood samples in a coagulation process are measured over time. The electrical characteristic measuring step (S502) can be performed by the measuring unit described in the above 1 (6).

In a result calculating step (S503), results regarding a blood coagulation inhibition ability of the inhibitor of the coagulation factor are calculated for each of the two blood samples on the basis of the measured electrical characteristics. The result calculating step (S503) can be performed by the result calculating unit described in the above 1 (6).

In a result comparing step (S504), the results calculated for each of the two blood samples are compared with each other. The result comparing step (S504) can be performed by the comparing unit described in the above 1 (6).

In a characteristic estimating step (S505), a characteristic regarding the inhibitor is estimated with reference to a correlation prepared in advance, on the basis of a comparison result. The characteristic estimating step (S505) can be performed by the estimating unit described in the above 1 (6).

6. Blood Loss Prediction Method

The present technology also provides a blood loss prediction method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of predicting a blood loss of an individual on the basis of a comparison result.

In the step of the comparing, the first result and the second result are compared with each other. The step of the comparing is the same as that of the comparing described the above 5., and a description thereof is thus omitted.

In the step of the predicting, the blood loss of the individual is predicted on the basis of the comparison result. All of the descriptions regarding the blood loss prediction apparatus according to the present technology in the above 2 are applied to the step of the predicting in the blood loss prediction method according to the present technology. That is, all of the descriptions of the comparison result mentioned with respect to the blood loss prediction apparatus according to the present technology and the prediction based on the comparison result are also applied to the step of the predicting. For this reason, these descriptions are omitted.

The blood loss prediction method according to the present technology may further include a step of acquiring various data used in the step of the comparing and the step of the predicting, if necessary. An example of such a step can include a step of adding the blood coagulation factor to the blood, a step of measuring an electrical characteristic of a blood sample, and a step of calculating a result regarding the blood coagulation inhibition ability of the inhibitor, but is not limited thereto. In these steps, the respective methods executed in the sample holding unit, the measuring unit, and the result calculating unit described in the above 1. can be performed.

An embodiment of the blood loss prediction method according to the present technology will be described with reference to a flowchart described in FIG. 7.

Figure 6:
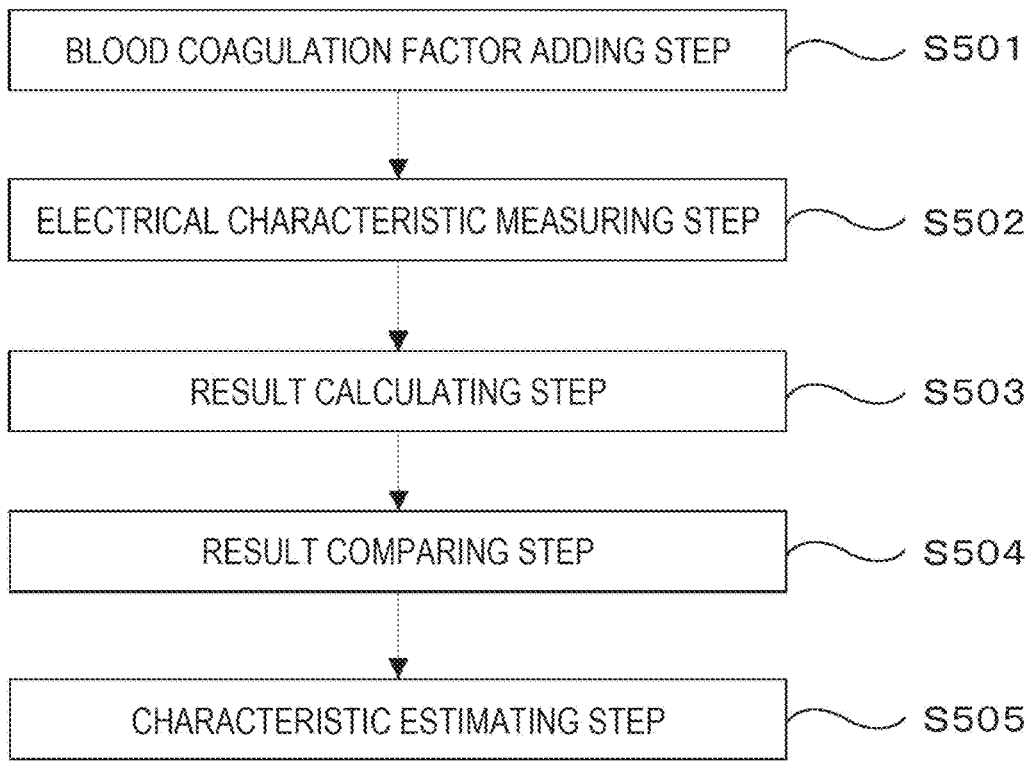
FIG. 6 is a flowchart of a blood coagulation system analysis method.
Figure 7:
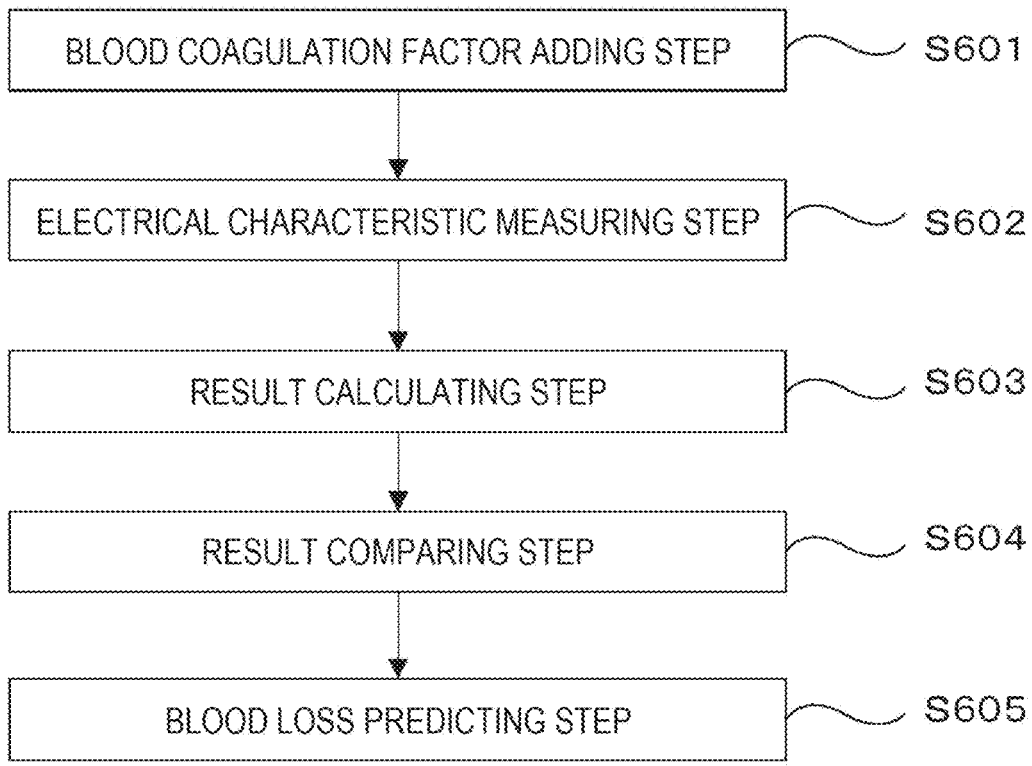
FIG. 7 is a flowchart of a blood loss prediction method.
Figure 8:
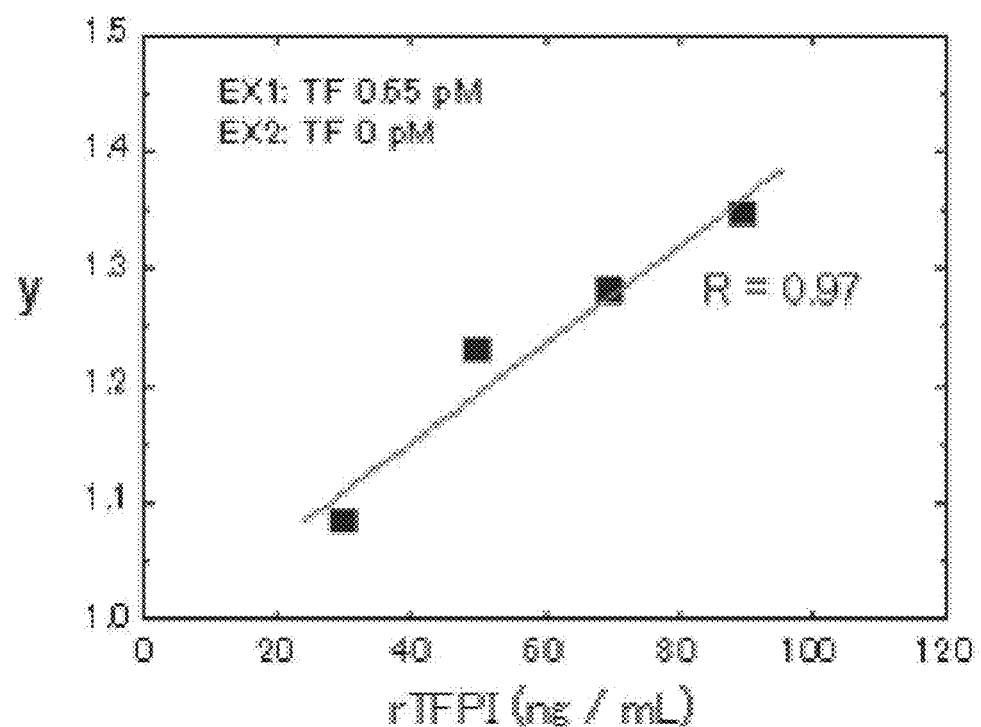
FIG. 8 is a graph illustrating a plot of a comparison result y with respect to a concentration of rTFPI.
Figure 9:
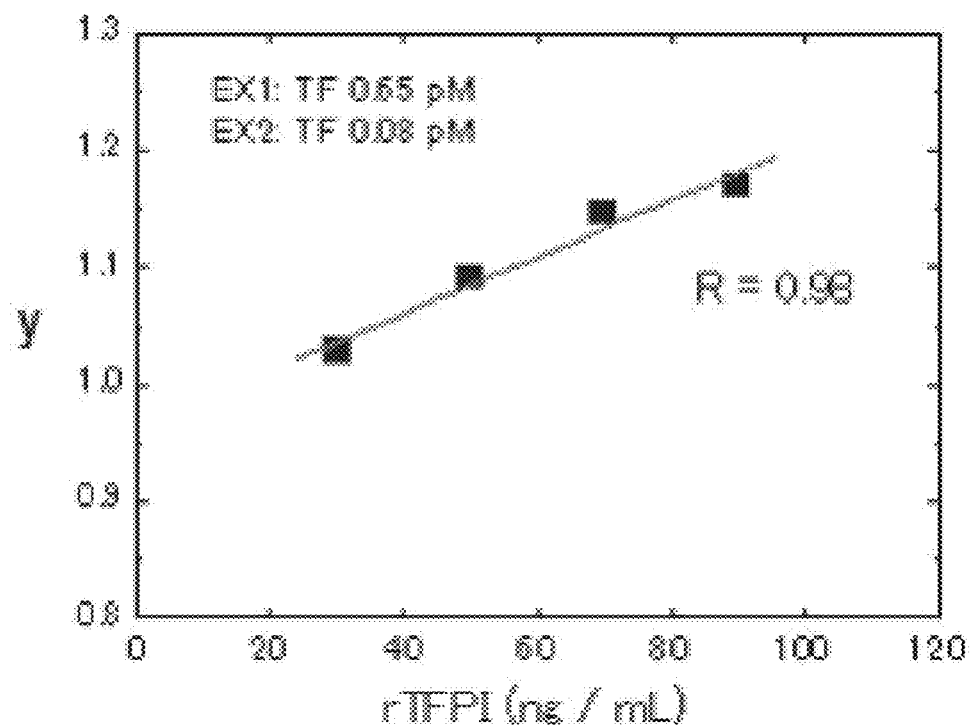
FIG. 9 is a graph illustrating a plot of a comparison result y with respect to a concentration of rTFPI.
Figure 10:
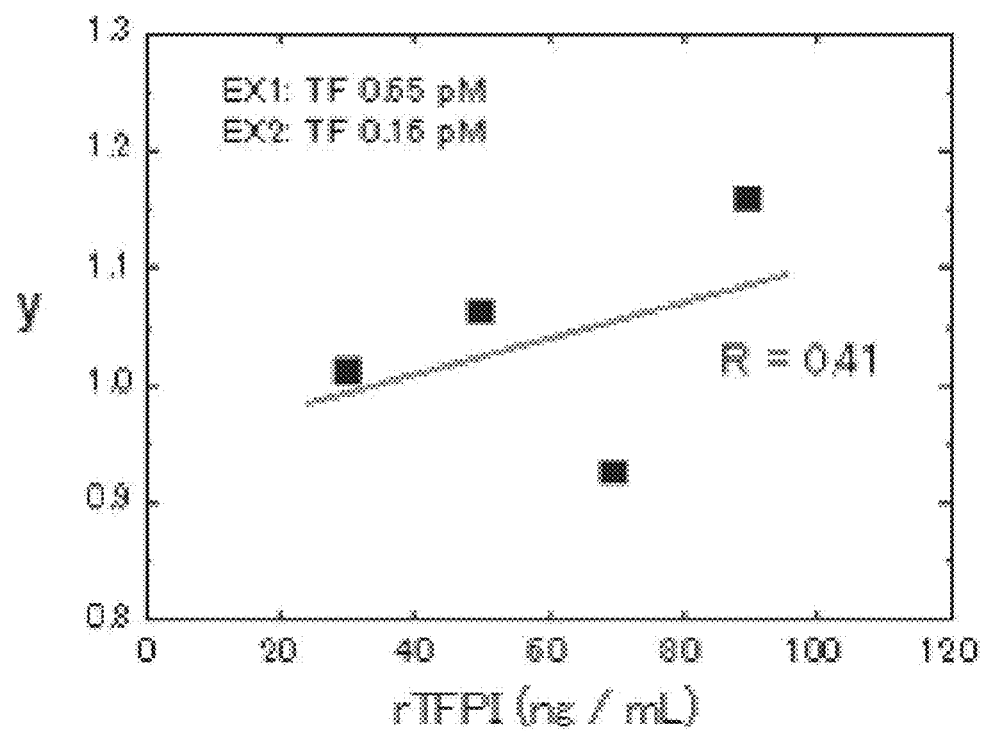
FIG. 10 is a graph illustrating a plot of a comparison result y with respect to a concentration of rTFPI.
Figure 11:
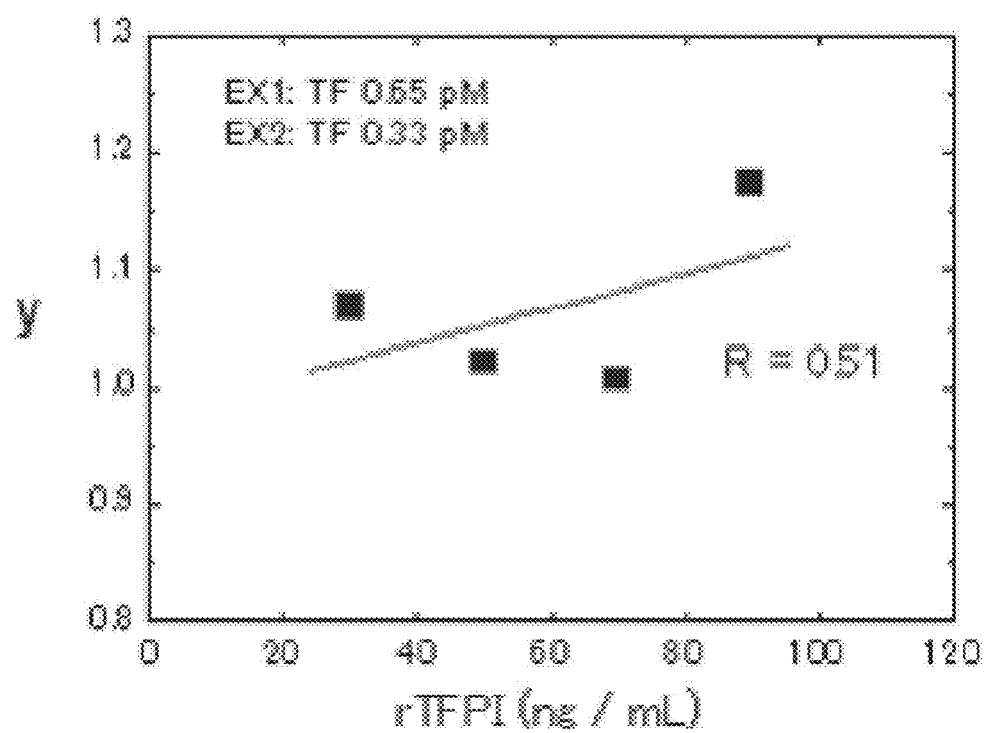
FIG. 11 is a graph illustrating a plot of a comparison result y with respect to a concentration of rTFPI.

Steps S601 to S604 in FIG. 7 correspond to steps S501 to S504 in FIG. 6, respectively, and a description thereof is thus omitted.

In a blood loss predicting step (S605), a blood loss of an individual is predicted with reference to a correlation prepared in advance, on the basis of a comparison result in step S604. The blood loss predicting step (S605) can be performed by the predicting unit described in the above 2.

7. Blood Coagulation System Analysis Program

The present technology also provides a blood coagulation system analysis program for causing a computer to execute: a step of estimating a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

The blood coagulation system analysis program according to the present technology is a program for causing the computer to execute the step of the estimating in the blood coagulation system analysis method according to the present technology described in the above 5. In addition, the blood coagulation system analysis program can be a program for causing the computer to execute the step of the comparing described in the above 5., if necessary. In addition, the blood coagulation system analysis program can be a program for causing the computer to execute a step of acquiring various data used in the step of the estimating. An example of such a step can include a step of adding the blood coagulation factor to the blood, a step of measuring an electrical characteristic of a blood sample, and a step of calculating a result regarding the blood coagulation inhibition ability of the inhibitor, but is not limited thereto. All of the steps executed by the blood coagulation system analysis program according to the present technology are the same as those described in the blood coagulation system analysis method according to the present technology, and a description thereof is thus omitted.

8. Blood Loss Prediction Program

The present technology also provides a blood loss prediction program for causing a computer to execute: a step of predicting a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

The blood loss prediction program according to the present technology is a program for causing the computer to execute the step of the predicting in the blood loss prediction method according to the present technology described in the above 6. In addition, the blood loss prediction program can be a program for causing the computer to execute the step of the comparing described in the above 6., if necessary. In addition, the blood loss prediction program can be a program for causing the computer to execute a step of acquiring various data used in the step of the predicting. An example of such a step can include a step of adding the blood coagulation factor to the blood, a step of measuring an electrical characteristic of a blood sample, and a step of calculating a result regarding the blood coagulation inhibition ability of the inhibitor, but is not limited thereto. All of the steps executed by the blood loss prediction program according to the present technology are the same as those described in the blood loss prediction method according to the present technology, and a description thereof is thus omitted.

The blood coagulation system analysis program and the blood loss prediction program according to the present technology may be stored in a recording medium such as a magnetic disk, an optical disk, a magneto-optical disk, or a flash memory, or may be distributed through a network.

EXAMPLE

9. Example 9-1. Correlation between Concentration of TFPI and Maximum Gradient in Permittivity Plot
(1) Outline of Experiment A plurality of blood samples were prepared by artificially adding a recombinant tissue factor pathway inhibitor (hereinafter, referred to as rTFPI) at different concentrations to blood of a healthy person in vitro. In a state where a tissue factor was added at different concentrations to each of the blood samples, coagulation pathways were activated to measure permittivities in a blood coagulation process over time. Measurement results were analyzed to obtain maximum gradients of changes in the permittivities for cases of each of the different concentrations of the tissue factors. When a ratio between the obtained maximum gradients was calculated, the ratio was changed depending on a concentration of rTFPI. Therefore, it was found that a concentration of TFPI in blood can be evaluated by the ratio. In addition, it was also found that evaluation can be more effectively performed in a case where a difference between the concentrations of the tissue factors of measurement used for analysis is large to some extent.

(2) Experiment Method

Venous blood of a healthy person was collected using a vacuum blood collection tube using citric acid as an anticoagulant. rTFPI available from Sigma-Aldrich Inc., was used. Since rTFPI was in a lyophilized state, rTFPI was dissolved so that a concentration thereof was 50 μg/mL according to a method recommended by a manufacturer to obtain an rTFPI solution. The rTFPI solution was added to the blood to prepare blood samples in which concentrations of rTFPI were 30, 50, 70 and 90 ng/mL, respectively. It should be noted that, in order to prevent a rate of dilution of the blood from being changed due to an amount of added rTFPI solution, normal saline was appropriately added to the blood samples so that the sum of amounts of rTFPI solution and normal saline was 1/10 of an amount of the blood in all of the blood samples.

Each of the blood samples was further divided into five, and a tissue factor (hereinafter, referred to as TF), which is an activator of an extrinsic coagulation pathway, was added at different concentrations to each of the five samples. The concentrations of TF in the five samples were 0, 0.08, 0.16, 0.33 and 0.65 pM, respectively, as final concentrations after TF was added. Calcium chloride was added to the five samples to remove an anticoagulant effect caused by citric acid. Permittivities, in a blood coagulation process, of the five samples in which the anticoagulant effect was removed were measured over time. An apparatus described in Japanese Patent Application Laid-Open No. 2016-045071 was used for measuring the permittivity. A frequency of an alternating voltage applied to the blood samples was 10 kHz to 10 MHz.

(3) Result

Maximum gradients of changes in the permittivities after blood coagulation started were calculated from measurement results. A ratio y between a maximum gradient in a case where the concentration of TF was 0.65 pM and a maximum gradient in a case where the concentration of TF was any of the other concentrations was calculated. y is represented by the following Equation 7.

[Equation 7]

$$y = CFR2_{EX1}/CFR2_{EX2} \qquad \text{Equation 7}$$

In Equation 7, $CFR2_{EX1}$ is the maximum gradient in the case where the concentration of TF was 0.65 pM. $CFR2_{EX2}$ is the maximum gradient in the case where the concentration of TF was any of the other concentrations. Results of plotting values of y based on the measurement results at a frequency of 10 MHz with respect to a concentration of rTFPI are illustrated in FIGS. 8 to 11. As illustrated in FIGS. 8 to 11, a correlation appeared between y and the concentration of rTFPI regardless a difference between the concentrations of TF, and a particularly good correlation appeared between y and the concentration of rTFPI particularly in a case where a difference between concentrations of TF was 0.57 pM and 0.65 pM.

In this manner, the concentration of TFPI in the blood can be estimated on the basis of the correlation between y and the concentration of TFPI.

9-2. Correlation Between Blood Loss and Maximum Gradient in Permittivity Plot
(1) Experiment Method Bloods of 18 adult patients who underwent cardiovascular surgery using an artificial heart-lung machine were collected at the time of the end of the cardiovascular surgery after closing the chest. In the cardiovascular surgery, heparin was neutralized by protamine during a period in which the artificial heart-lung machine was operated. Citric acid was added as an anticoagulant to the obtained bloods. In addition, a blood loss from a drain for postoperative 48 hours was measured.

Each of the bloods was further divided into two blood samples, TF was added to one of the two blood samples, but was not added to the other of the two samples, and permittivities, in a blood coagulation process, of the blood sample to which TF was added and the blood sample to which TF was not added were measured over time. A concentration of TF in the blood to which TF was added was 0.65 pM as a final concentration after TF was added. An apparatus described in Japanese Patent Application Laid-Open No. 2016-045071 was used for measuring the permittivity. A frequency of an alternating voltage applied to the blood samples was 10 MHz. An anticoagulant effect caused by citric acid was removed by adding calcium chloride. In addition, a hematocrit value of the blood was measured by a method of calculating a hematocrit value on the basis of a complex permittivity as described in International Publication No. WO 2014/141844.

(2) Result

Maximum gradients of changes in the permittivities after blood coagulation started were calculated from measurement results. y was calculated by correcting a ratio between a maximum gradient in a case where the concentration of TF was 0.65 pM and a maximum gradient in a case where TF was not added (that is, in a case where in the concentration of TF was 0 pM) by the hematocrit value. y is represented by the following Equation 8.

[Equation 8]

$$y = \frac{CFR2_{EX1}(100 - Hct)}{CFR2_{EX2}} \qquad \text{Equation 8}$$

Figure 12:
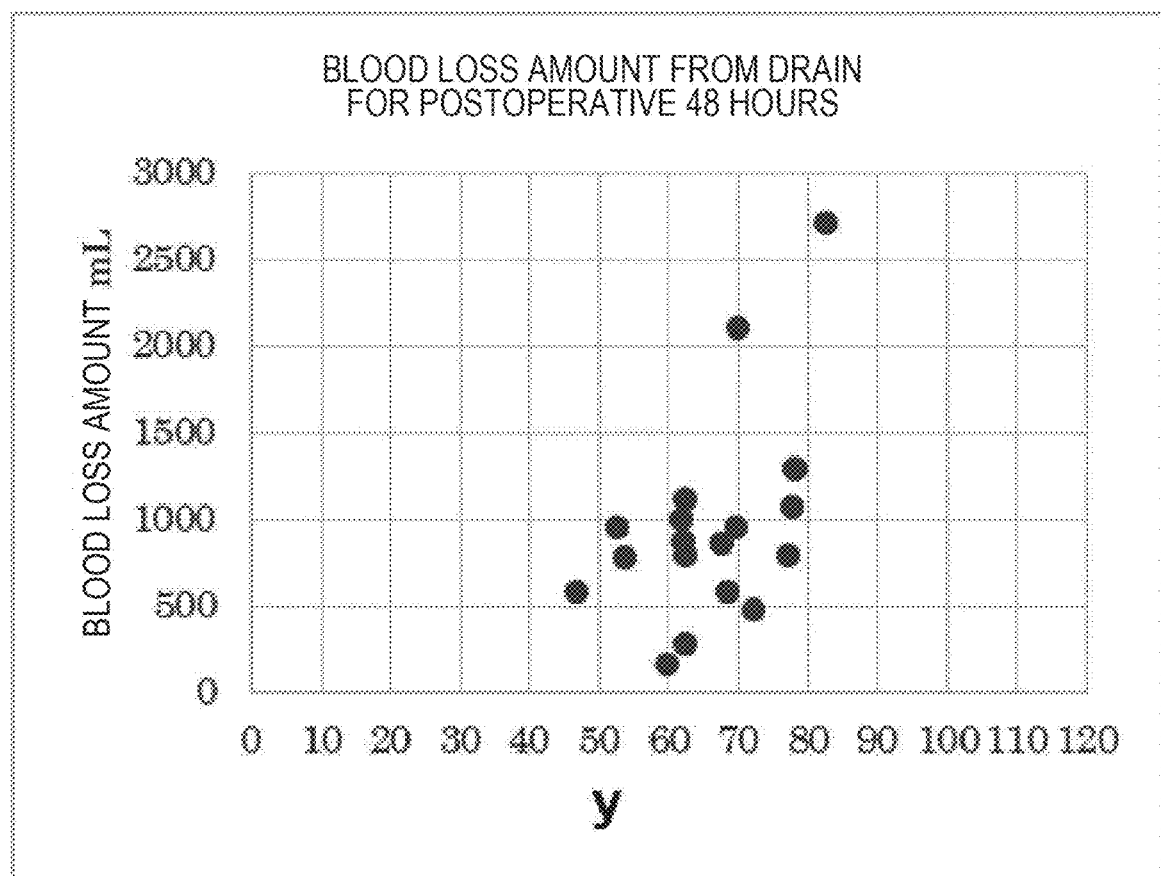
FIG. 12 is a graph illustrating a plot of a comparison result y with respect to a postoperative blood loss.

In Equation 8, $CFR2_{EX1}$ is the maximum gradient in the case where the concentration of TF was 0.65 pM. $CFR2_{EX1}$ is the maximum gradient in the case where TF was not added. Hct is the hematocrit value (%). A result of plotting values of y with respect to a postoperative blood loss is illustrated in FIG. 12. As illustrated in FIG. 12, a correlation appeared between y and the postoperative blood loss (a correlation coefficient by a Spearman test was 0.5).

In this manner, the postoperative blood loss can be predicted on the basis of the correlation between y and the postoperative blood loss.

It should be noted that the present technology can also adopt the following configuration.

[1] A blood coagulation system analysis apparatus including: an estimating unit that estimates a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

[2] The blood coagulation system analysis apparatus according to the above [1], in which the first result and the second result are rates of change of the electrical characteristic at a point in time when a change over time in the electrical characteristic becomes maximum after blood coagulation starts.

[3] The blood coagulation system analysis apparatus according to the above [1] or [2], in which the comparison result is a ratio between the first result and the second result.

[4] The blood coagulation system analysis apparatus according to any one of the above [1] to [3], in which a difference between the concentration of the blood coagulation factor in the blood from which the first result is obtained and the concentration of the blood coagulation factor in the blood from which the second result is obtained is 0.50 pM or more.

[5] The blood coagulation system analysis apparatus according to any one of the above [1] to [4], in which the inhibitor is a tissue factor pathway inhibitor.

[6] The blood coagulation system analysis apparatus according to any one of the above [1], [2], [4] and [5], in which the comparison result is a result obtained by correcting a ratio between the first result and the second result by a hematocrit value of the blood.

[7] The blood coagulation system analysis apparatus according to any one of the above [1], [2], [4] and [5], in which the comparison result is a result obtained by correcting a ratio between the first result and the second result by a hematocrit value of the blood and a characteristic value regarding an intrinsic coagulation pathway.

[8] The blood coagulation system analysis apparatus according to any one of the above [1] to [7], in which the characteristic regarding the inhibitor is a concentration or an activity of the inhibitor.

[9] A blood loss prediction apparatus including: a predicting unit that predicts a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

[10] A blood coagulation system analysis system including: a blood coagulation system analysis apparatus that includes an estimating unit estimating a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a display apparatus that displays an estimation result.

[11] A blood loss prediction system including: a blood loss prediction apparatus that includes a predicting unit predicting a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a display apparatus that displays the predicted blood loss.

[12] A blood coagulation system analysis method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of estimating a characteristic regarding the inhibitor on the basis of a comparison result.

[13] A blood loss prediction method including: a step of comparing a first result regarding a blood coagulation inhibition ability of an inhibitor of a blood coagulation factor and a second result regarding the blood coagulation inhibition ability with each other, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added; and a step of predicting a blood loss of an individual on the basis of a comparison result.

[14] A blood coagulation system analysis program for causing a computer to execute: a step of estimating a characteristic regarding an inhibitor of a blood coagulation factor on the basis of a comparison result between a first result regarding a blood coagulation inhibition ability of the inhibitor of the blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

[15] A blood loss prediction program for causing a computer to execute: a step of predicting a blood loss of an individual on the basis of a comparison result between a first result regarding a blood coagulation inhibition ability of an inhibitor of a blood coagulation factor and a second result regarding the blood coagulation inhibition ability, the first result being obtained on the basis of at least one electrical characteristic of blood to which the blood coagulation factor is added, and the second result being obtained on the basis of at least one electrical characteristic of the blood to which the blood coagulation factor is added so that a concentration of the blood coagulation factor is different from a concentration of the blood coagulation factor in the blood to which the blood coagulation factor is added or the blood coagulation factor is not added.

REFERENCE SIGNS LIST

100 Blood coagulation system analysis apparatus
101 Estimating unit
102, 202 Sample holding unit
103, 203 Measuring unit
104, 204 Result calculating unit
105, 205 Comparing unit
106, 206 Display unit
200 Blood loss prediction apparatus
201 Predicting unit
300 Blood coagulation system analysis system
301 Blood coagulation system analysis apparatus
302 Display apparatus
400 Blood loss prediction system
401 Blood loss prediction apparatus
402 Display apparatus

The invention claimed is:

1. A blood coagulation system analysis apparatus comprising:
an estimating unit that estimates a characteristic regarding an inhibitor of a blood coagulation factor on a basis of a comparison result between a first result regarding a blood coagulation inhibition ability of the inhibitor of the blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor.

2. The blood coagulation system analysis apparatus according to claim 1, wherein the first result and the second result are rates of change of the at least one electrical characteristic at a point in time when a change over time in the at least one electrical characteristic becomes maximum after blood coagulation starts.

3. The blood coagulation system analysis apparatus according to claim 1, wherein the comparison result is a ratio between the first result and the second result.

4. The blood coagulation system analysis apparatus according to claim 1, wherein a difference between the concentration of the blood coagulation factor in the first blood sample from which the first result is obtained and the concentration of the blood coagulation factor in the second blood sample from which the second result is obtained is 0.50 pM or more.

5. The blood coagulation system analysis apparatus according to claim 1, wherein the inhibitor is a tissue factor pathway inhibitor.

6. The blood coagulation system analysis apparatus according to claim 1, wherein the comparison result is a result obtained by correcting a ratio between the first result and the second result by a hematocrit value of the blood.

7. The blood coagulation system analysis apparatus according to claim 1, wherein the comparison result is a result obtained by correcting a ratio between the first result and the second result by a hematocrit value of the blood and a characteristic value regarding an intrinsic coagulation pathway.

8. The blood coagulation system analysis apparatus according to claim 1, wherein the characteristic regarding the inhibitor is a concentration or an activity of the inhibitor.

9. A blood loss prediction apparatus comprising:
a predicting unit that predicts a blood loss of an individual on a basis of a comparison result between a first result regarding a blood coagulation inhibition ability of an inhibitor of a blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor.

10. A blood coagulation analysis system comprising:
a blood coagulation system analysis apparatus that includes an estimating unit estimating a characteristic regarding an inhibitor of a blood coagulation factor on a basis of a comparison result between a first result regarding a blood coagulation inhibition ability of the inhibitor of the blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor; and a display apparatus that displays an estimation result.

11. A blood loss prediction system comprising:

a blood loss prediction apparatus that includes a predicting unit predicting a blood loss of an individual on a basis of a comparison result between a first result regarding a blood coagulation inhibition ability of an inhibitor of a blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor; and a display apparatus that displays the predicted blood loss.

12. A blood coagulation system analysis method comprising:

comparing a first result regarding a blood coagulation inhibition ability of an inhibitor of a blood coagulation factor and a second result regarding the blood coagulation inhibition ability with each other, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor; and estimating a characteristic regarding the inhibitor on a basis of a comparison result.

13. A blood loss prediction method comprising:

comparing a first result regarding a blood coagulation inhibition ability of an inhibitor of a blood coagulation factor and a second result regarding the blood coagulation inhibition ability with each other, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor; and predicting a blood loss of an individual on a basis of a comparison result.

14. A non-transitory computer readable medium storing instructions that, when executed by a computer, perform a blood coagulation system analysis method comprising: estimating a characteristic regarding an inhibitor of a blood coagulation factor on a basis of a comparison result between a first result regarding a blood coagulation inhibition ability of the inhibitor of the blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor.

15. A non-transitory computer readable medium storing instructions that, when executed by a computer, perform a blood loss prediction method comprising: predicting a blood loss of an individual on a basis of a comparison result between a first result regarding a blood coagulation inhibition ability of an inhibitor of a blood coagulation factor and a second result regarding the blood coagulation inhibition ability, the first result being obtained on a basis of at least one electrical characteristic of a first blood sample to which the blood coagulation factor is added, and the second result being obtained on a basis of at least one electrical characteristic of a second blood sample, wherein the second blood sample contains either a concentration of the blood coagulation factor which is different from a concentration of the blood coagulation factor in the first blood sample or does not contain any blood coagulation factor.

* * * * *